United States Patent [19]
Vogler et al.

[11] Patent Number: 5,378,431
[45] Date of Patent: Jan. 3, 1995

[54] DUAL PATHWAY CLOTTING ENHANCER FOR BLOOD COLLECTION TUBE

[75] Inventors: Erwin A. Vogler, Newhill; Jane C. Graper, Durham, both of N.C.

[73] Assignee: Becton, Dickinson and Company, Franklin Lakes, N.J.

[21] Appl. No.: 76,521

[22] Filed: Jun. 14, 1993

[51] Int. Cl.[6] ............................................. G01N 33/00
[52] U.S. Cl. .................................... 422/73; 422/57; 422/101; 422/102; 436/69; 435/13
[58] Field of Search ................. 422/73, 101, 102, 57; 436/69; 435/2, 13

[56] References Cited

U.S. PATENT DOCUMENTS

| | | | |
|---|---|---|---|
| 4,153,739 | 8/1979 | Kessler | 427/2 |
| 4,257,886 | 3/1981 | Kessler | 210/516 |
| 4,579,828 | 4/1986 | Ali | 422/73 |
| 4,608,997 | 9/1986 | Conway | 128/763 |
| 5,019,243 | 5/1991 | McEwen et al. | 422/102 |
| 5,039,617 | 8/1991 | McDonald et al. | 436/69 |
| 5,089,422 | 2/1992 | Brubaker | 436/69 |
| 5,169,786 | 12/1992 | Carroll et al. | 436/69 |
| 5,246,666 | 9/1993 | Vogler et al. | 422/101 |

OTHER PUBLICATIONS

Hemostasis and Coagulation in Hematology: Principles and Procedures, Third Edition, Lea and Febiger, Philadelphia, Pa. 1980, pp. 113–119.

*Primary Examiner*—Donald E. Czaja
*Assistant Examiner*—Lien Tran
*Attorney, Agent, or Firm*—Richard E. Brown

[57] ABSTRACT

A blood collection assembly includes a container, optionally covered by a puncturable septum and evacuated. A clotting enhancer in the container activates both the intrinsic and extrinsic coagulation pathways.

10 Claims, 7 Drawing Sheets

DUAL PATHWAY CLOTTING ENHANCER FOR BLOOD COLLECTION TUBE

BACKGROUND OF INVENTION

1. Field of the Invention

This invention relates to blood collection and more particularly relates to an additive for a collection tube which enhances clotting.

2. Background

Blood samples are routinely taken in evacuated tubes, such as glass VACUTAINER ™ tubes (Becton, Dickinson and Company). One end of a double-ended needle is inserted into a patient's vein. The other end of the needle then punctures a septum covering the open end of the VACUTAINER ™, tube so that the vacuum in the tube draws the blood sample through the needle into the tube. Using this technique, a plurality of samples can be taken using a single needle puncture of the skin. Plastic tubes have also been proposed for blood collection. Plastic offers a number of advantages such as lower breakage than glass tubes, less weight in shipment, and easier disposal by incineration.

Blood collected in evacuated tubes often must be clotted prior to clinical examination. It is desirable to form a dense clot as rapidly and completely as possible to facilitate clean separation of the clot from the serum layer by centrifugation. To achieve this end, both plastic and glass blood collection tubes frequently employ a clot activator.

Two types of activators, classified in the art according to the portion of the blood coagulation cascade stimulated, are conventionally employed. Particulate activators share a common biochemical mechanism of clot activation known as contact activation of the intrinsic pathway. Whole blood contains all of the necessary factors to cause clotting by the intrinsic pathway. Clot activation by the intrinsic pathway is surface area dependent, i.e., the time required to form a complete blood clot is dependent on the total number of activating surface sites per unit-area on the activator surface relative to the volume of blood. Greater surface area, provided by finely divided particulate activators, leads to shorter clot times. Particulate activators are used in practically all commercial blood collection tubes and lead to dense, crosslinked clots that cleanly separate from the serum in a hematological centrifuge. Clot formation, however, is relatively slow, and about 30–60 minutes are required prior to centrifugation. Typical particulate activators used commercially are silica impregnated in fabric, silica particles in small plastic cups or silicate particles applied to the tube wall in polyvinylpyrrolidone (PVP). When blood enters a tube containing silicate-PVP, the PVP dissolves, enters the serum and the silicate particles are released.

The second type of clot activators induces clotting through a different part of the coagulation cascade known in the art as the extrinsic pathway. The extrinsic system relies on the presence of a substance not normally present in whole blood. Activation is biochemical in nature and is concentration dependent. Clot activation rates are very high, leading to clot formation in 10–20 minutes, but clots resulting from the extrinsic pathway are gelatinous in nature and do not cleanly separate from serum. With extrinsic pathway activators, serum quality is frequently poor and may not meet the needs of sensitive clinical analysis. Further, contamination of serum by externally added blood-soluble protein activators is undesirable.

There is a need in the art for a clot activating additive for a blood collection tube which rapidly provides a dense clot which separates clearly from the serum without contaminating the serum with soluble chemicals which may interfere with blood analyses. The present invention is directed to fulfilling this need.

SUMMARY OF THE INVENTION

A blood collection assembly includes a blood collection container, preferably covered with a puncturable septum and evacuated. The container has a coagulation rate enhancer therein which activates both the intrinsic and extrinsic blood coagulation pathways. The preferred enhancer is a glass particle having a surface area of the native, unmodified glass which activates the intrinsic coagulation pathway. A second surface area of the particle has an activator of the extrinsic pathway immobilized thereon, preferably on a plastic coating. In another aspect of the invention, a method to prepare the coagulation rate enhancer is provided. The activator of the extrinsic pathway is immobilized on the surface of a hollow glass microsphere. The coated microsphere may be combined with an unmodified glass microsphere, the native glass surface of which activates the intrinsic pathway. In a preferred method, the coated microsphere is crushed to expose the unmodified interior glass surface and provide a particle having both coated and uncoated surfaces.

Thus the blood collection assembly of the invention, in providing activation of both the intrinsic and extrinsic coagulation pathways, is ideally suited for collection of blood samples from which a clear serum layer free of extraneous particulate or soluble activators is to be generated by centrifugation.

DETAILED DESCRIPTION

While this invention is satisfied by embodiments in many different forms, there will herein be described in detail preferred embodiments of invention with the understanding that the present disclosure is to be considered as exemplary of the principles of the invention and is not intended to limit the invention to the embodiments illustrated and described. The scope of the invention will be measured by the appended claims and their equivalents.

The blood collection assembly of the invention may include any container having the dual pathway activator of the invention therein. The container may have continuous bottom and side walls defining a closed end and open end respectively. The bottom wall and the side wall together define an inside wall surface. Suitable containers are, for example bottles, vials, flasks and the like, preferably tubes. The invention will henceforth be described in terms of the preferred tube.

The tube may preferably be combined with a puncturable septum over the open end and may be evacuated. Evacuated tubes for blood collection are standard in the art as, for example, VACUTAINER ™ brand tubes (Becton, Dickinson and Company).

Figure 1:
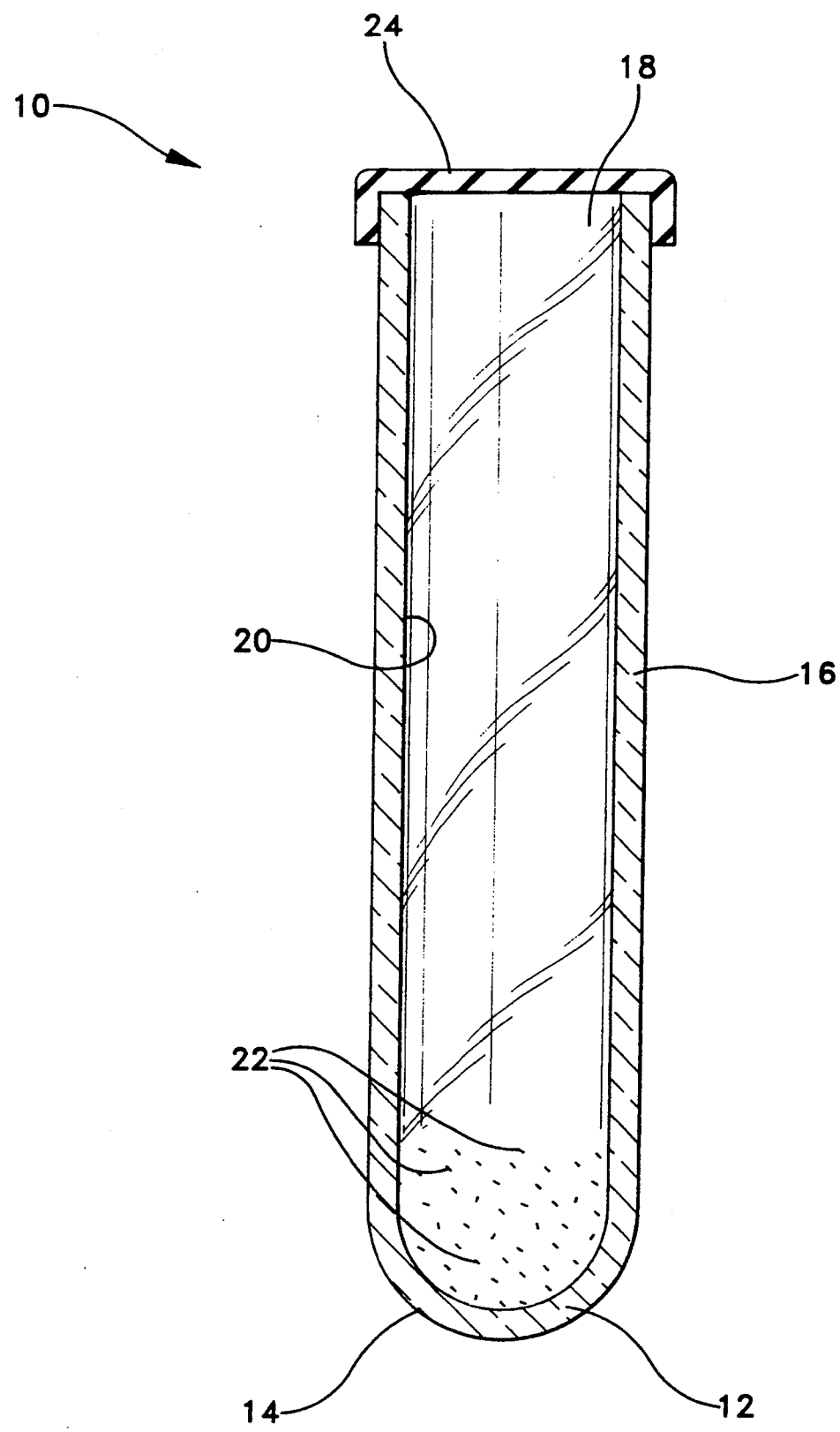
FIG. 1 is a perspective view of the blood collection assembly of the invention.

FIG. 1 illustrates the tube of the invention. A tube 10 has a bottom wall 12 defining a closed end 14 and a side wall 16 defining an open end 18. Bottom wall 12 and side wall 16 are continuous and together define an inside wall surface 20. A multiplicity of dual pathway activating particles 22 (illustrated in detail in FIG. 2) are placed in tube 10. The open end 18 of tube 10 is covered with puncturable septum 24.

The tube may be of glass or preferably plastic. Suitable plastics are polyvinyl chloride, polypropylene (PP), polyethylene terephthalate (PET) and preferably polystyrene (PS).

The invention contemplates any activator of the extrinsic pathway, such as ellagic acid, or preferably a protein, most preferably thrombin, heparinase and fibrinogen. In one embodiment of the invention, the inside wall surface of the tube itself may serve as the enhancer. Thus, if the tube is glass, an area of the native glass surface may activate the intrinsic pathway and the activator of the extrinsic pathway may be immobilized on a second surface area. Any conventional method may be used to immobilize the extrinsic activator. In one method, the activator is covalently conjugated to polar functional groups on the glass surface. In another method, a coating of polymer is applied to the second surface area, preferably to the bottom portion of the tube, and the activator is absorbed thereon. Conjugation and absorption procedures are well known to those skilled in the art and no further details are needed for a full understanding of this aspect of the invention.

If the tube is plastic, an inside wall surface area, preferably at the tube bottom, may have the extrinsic activator immobilized thereon, preferably by absorption of the protein activator on the plastic, as described above. A second inside wall surface area may be modified chemically to serve as activator of the intrinsic pathway. Suitable reagents are chromic and sulfuric acids whereby the polymer structure is attacked by the acid with introduction of polar groups which activate the intrinsic pathway. In a preferred embodiment of the invention, the coagulation enhancer is a particle in the tube which activates both the intrinsic and extrinsic coagulation pathways. The particle may be a glass particle having a surface area of the native (unmodified) glass which serves as activator of the intrinsic coagulation pathway. A second surface area of the glass particle may have an activator of the extrinsic coagulation pathway immobilized thereon. The particle may be of any shape, such as beads, cover slips and the like. The most preferred particle is a hollow glass microsphere. A suitable microsphere which is commercially available is the product sold under the trade name SCOTCHLITE ™ by 3M Corporation, Minneapolis, Minn. This product has about 0.7 m$^2$ surface area/gram.

Coating of the glass microsphere with the extrinsic activator may be done by any of the conventional procedures described above for coating the inside wall surface of the glass tube. A preferred method includes a coating of polymer, as described in Example II B. The extrinsic activator may be immobilized on the glass or plastic surface at a concentration of about 1 to 10, preferably about 5 mg/m$^2$ of surface. The glass microspheres having the immobilized activator of the extrinsic coagulation pathway thereon may be combined with unmodified microspheres whereby the mixture of coated and uncoated particles activate the extrinsic and intrinsic coagulation pathways respectively. The coated and uncoated particles may be combined in any proportion desired to get any ratio of activation of the two pathways. Preferably the ratio may be from about 20/80 to 80/20 most preferably about 50/50.

Alternatively and preferably, the coated microspheres may be crushed whereby the native unmodified glass surface of the inside wall surface of the microspheres is exposed, and the ratio of surface areas of intrinsic and extrinsic activating surfaces is 50/50. The microspheres crush easily and crushing may conveniently be done in a mortar and pestle. The size of the crushed particles is not critical and may be controlled at the manufacturing stage to give any desired particle size range. The crushed particles have about 0.9 m$^2$ of surface area/gram of both inside and outside surface.

Any colloidal or floating uncrushed particles may easily be removed by flotation.

Figure 2:
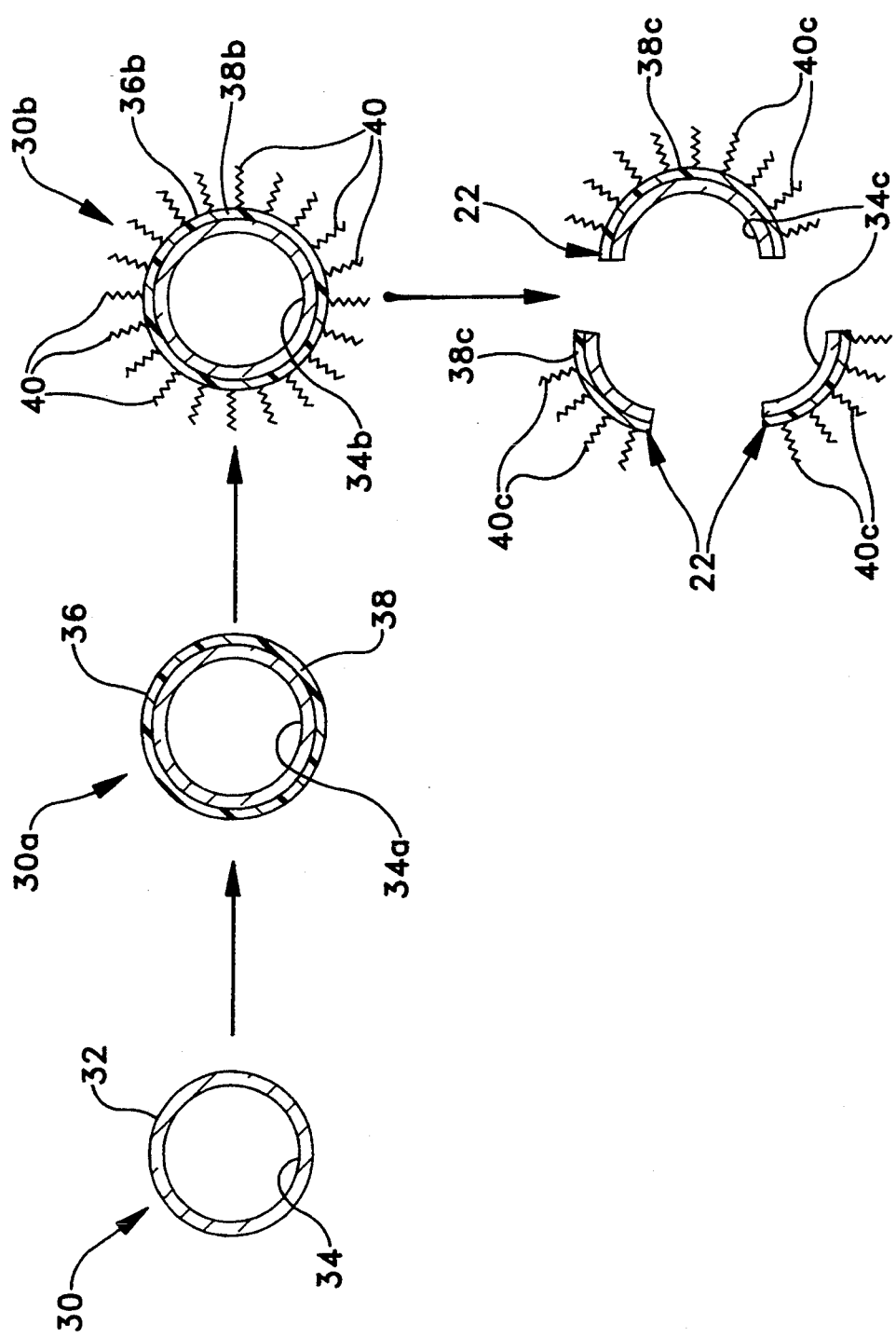
FIG. 2 is a schematic representation of a method for preparation of a preferred activator of the invention.

FIG. 2 illustrates the crushed microspheres of the invention, and the procedure for their manufacture. In FIG. 2, elements substantially the same or similar to elements described earlier are given the same reference number followed by a letter suffix. A glass microsphere 30 has outside wall surface 32 and inside wall surface 34. Microsphere 30 may be modified by applying a coating 36 of plastic over outside wall surface 32 to give coated microsphere 30a having glass inside wall surface 34a and plastic outside wall surface 38. Microsphere 30a may then be further modified to give microsphere 30b having glass inside wall surface 34b, plastic coating 36b having outside wall surface 38b and extrinsic pathway activator 40 immobilized on surface 38b. Microsphere 30b may then be crushed to give a plurality of dual pathway activating particles 22 having glass inside wall surface 34c which activates the intrinsic coagulation pathway, plastic outside wall surface 38c and extrinsic pathway activator 40c immobilized on surface 38c.

Many patient blood samples contain an anticoagulant such as citric acid, heparin or ethylenediaminetetraacetic acid (EDTA). In accordance with the invention, the enhancer may include an antagonist for the anticoagulant in addition to the activator for the extrinsic pathway. Immobilized heparinase or thrombin, enzymes which deactivate heparin, may fill both roles. The embodiments of the invention which include a layer of plastic provide a dual clinical functionality in that blood clots adhere strongly to the plastic surface but do not adhere to the glass or chemically modified plastic regions. Thus, when a blood sample taken in the tube of the invention is centrifuged, the blood clots at the glass or chemically modified plastic region and the clot flows, pellets and adheres to the plastic region. A clear serum layer forms above the clot with no fibrin rings and strands or activator particles suspended in the serum or adhering to the upper region of the tube. The strong adherence of the clot to the plastic region prevents mechanical remixing of clot and serum when the centrifuged tube is handled or transported.

EXAMPLE I

Preparation of Tubes for Coagulation Studies

Platelet poor plasma (PPP) was prepared by separating cells by centrifugation of citrated porcine blood (Environmental Diagnostics Inc). Approximately 0.5 ml of PPP was added to polystyrene test tubes (Becton Dickinson, 13 mm by 75 mm) containing known weight of test activators end equilibrated to room temperature in a water bath for 15 minutes. Following equilibration, 200 ul of 0.2M $CaCl_2$ per ml of PPP were added to initiate coagulation. Tube contents were mixed on a laboratory inverting mixer and time of clotting noted for each tube. Clotted PPP was distinguished from nonclotted PPP by an obvious change from a fluid state to a gelatinous state which did not flow in the tube upon rotation. Clotting time was measured at this point.

EXAMPLE II

Immobilization of Activators of Extrinsic Coagulation Pathway

A. Commercial hollow glass microspheres were obtained from 3M Corporation, SCOTCHLITE TM brand (0.7 $m^2$ surface area/gram as determined by Krypton gas adsorption, Porous Materials Inc., Ithaca, N.Y.).

Figure 3:
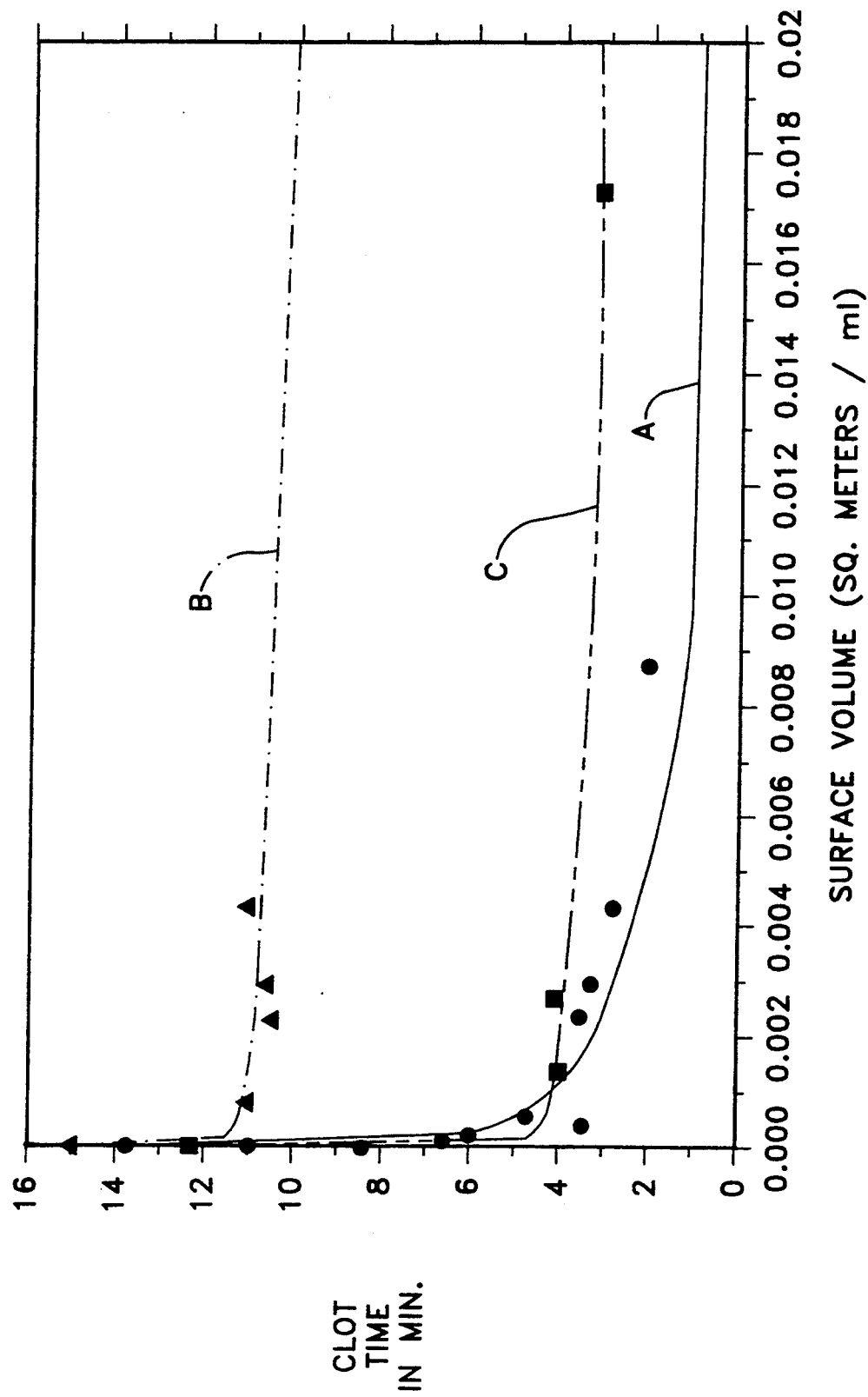
FIGS. 3–7 are plots of clot time against the ratio of blood sample volume to activator surface area for various embodiments of the invention.

B. Surfaces of the hollow glass spheres of A were passivated to clot activation by silane treatment with 2% octadecyltrichlorosilane, OTS, (Hulls America) in chloroform for 60 minutes, washed in solvent and water arid then air dried before weighing into test tubes. C. The OTS-treated glass spheres of B were added to a 1 mg/ml solution of bovine thrombin (Sigma) in phosphate buffered saline (Gibco) and mixed for one hour on a laboratory inverting mixer. The glass spheres having immobilized thrombin thereon were washed rigorously 3× in saline to remove unbound thrombin and air dried before weighing into test tubes. Clotting times were recorded for the unmodified glass spheres of A (activator of the intrinsic pathway), the OTS coated glass spheres of B and the glass spheres of C having thrombin (activator of the extrinsic pathway) immobilized on the OTS coating. The results of this experiment are shown in FIG. 3 in which clot time is plotted against the ratio of surface area of the spheres to volume of PPP. Curve A demonstrates clot activation of the intrinsic pathway of the coagulation pathway by the untreated high-surface-energy glass spheres. Curve B shows that the low surface energy OTS coating rendered the spheres substantially non-clot activating. Curve C shows that immobilized thrombin causes about a 3-fold decrease in clotting time relative to the OTS coated spheres of B lacking thrombin. It is seen that clot time precipitously decreases with small added amount of surface-immobilized thrombin to a plateau clot time around 4 minutes, suggesting that this immobilized enzyme system was substrate limited near $2 \times 10^{-3}$ $m^2$/ml surface-to-volume ratio. By contrast, untreated glass spheres exhibited a continuously-decreasing clot time with added activator.

EXAMPLE III

This example measures the enzymatic activity of the immobilized thrombin of Example II by direct comparison to the clot activity of soluble thrombin.

Figure 4:
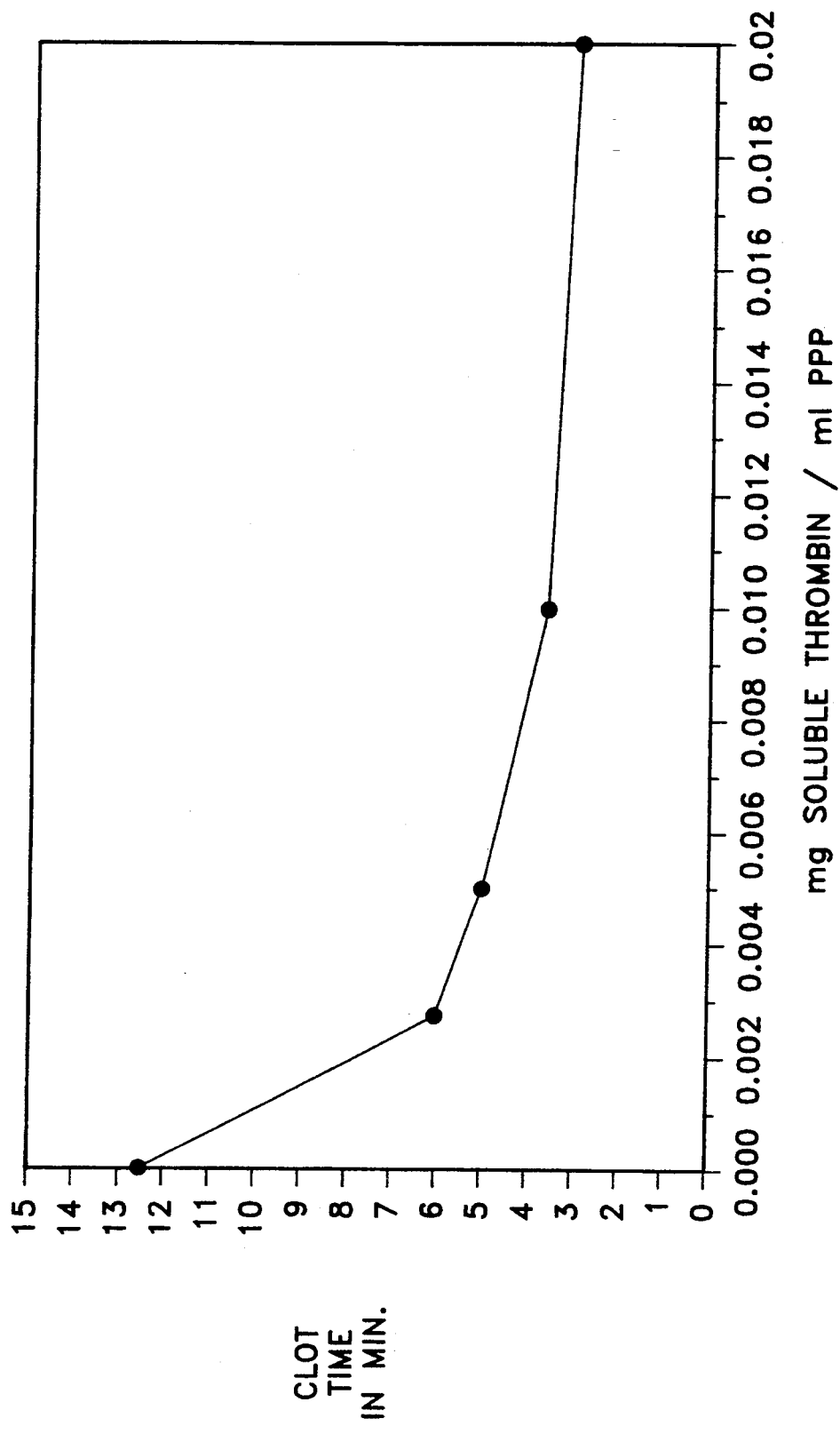

FIG. 4 shows PPP clot time observed at different soluble thrombin concentrations. It is seen that FIG. 4 is similar to curve C of FIG. 3, especially with respect to the attainment of a plateau limit in clot time observed near 4 minutes. Thus $1 \times 10^{-2}$ mg/ml soluble thrombin (4 minute limit from FIG. 4) is roughly equivalent to the enzymatic activity obtained with surface-immobilized thrombin near $1 \times 10^{-3}$ $m^2$/ml (estimated from curve C of FIG. 3). From this data, an effective active-enzyme loading on the OTS-treated glass spheres may be estimated to be $1 \times 10^{-2}$ mg on $2 \times 10^{-3}$ $m^2$ surface area, or about 5 mg/$m^2$.

EXAMPLE IV

This example demonstrates that soluble thrombin exhibits heparin antagonistic properties.

Figure 5:
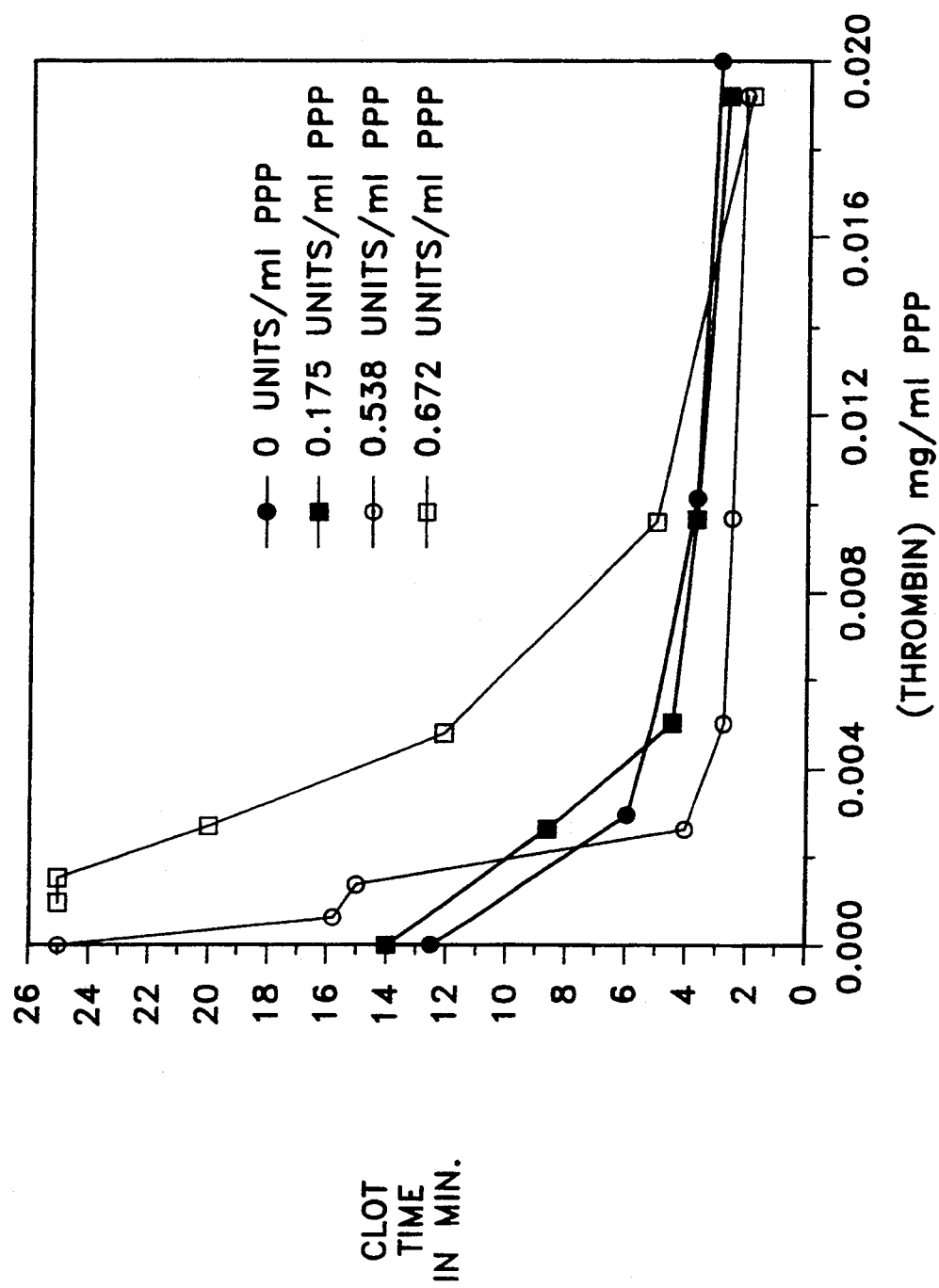

Tubes were prepared as in Example I containing different concentrations of soluble heparin, and various concentrations of soluble thrombin. It is seen from FIG. 5 that increasing concentrations of clotactivating thrombin are required to clot PPP containing increasing amounts of heparin.

EXAMPLE V

This example demonstrates that surface-immobilized thrombin of Example II C exhibits heparin antagonistic activity.

Figure 6:
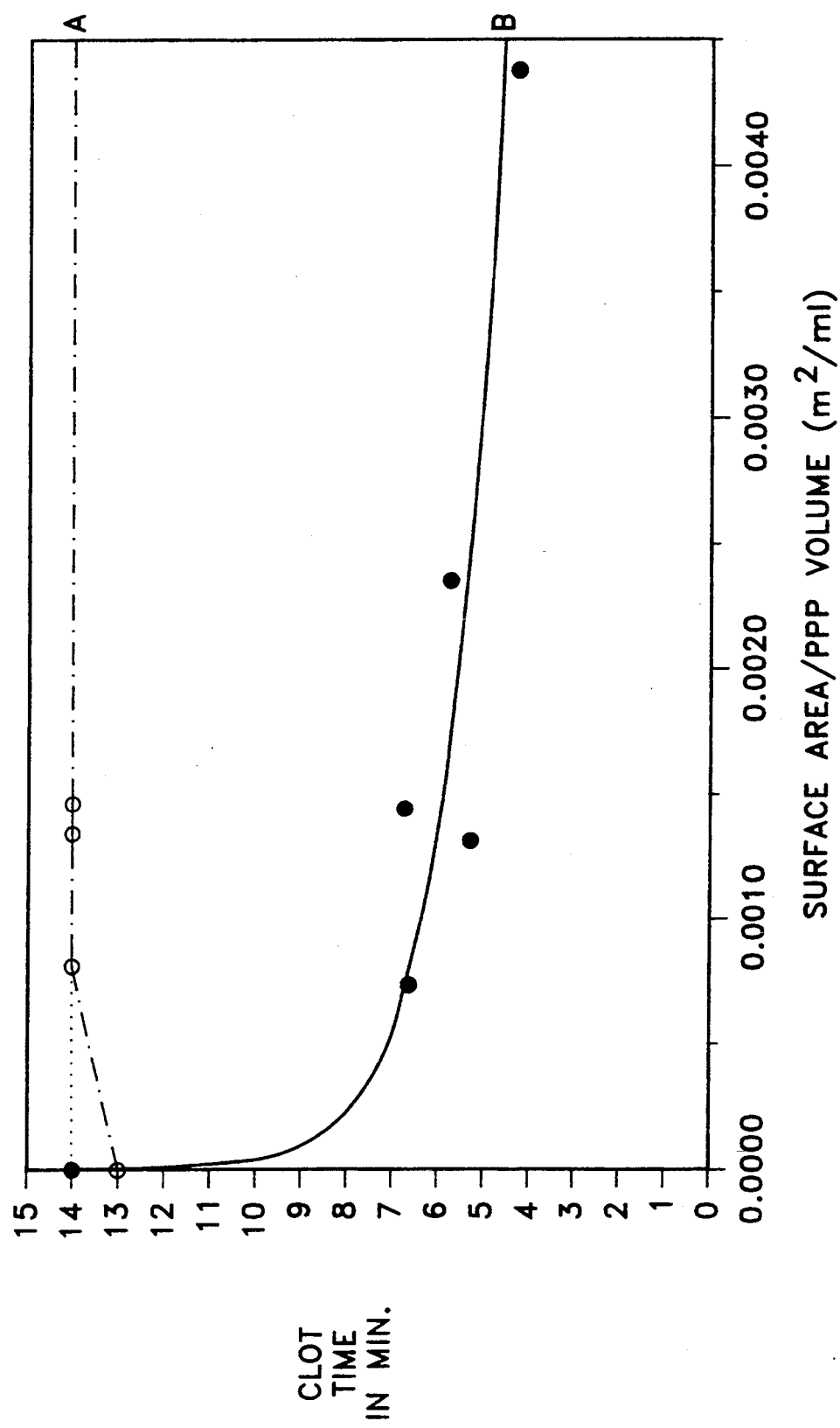

Tubes in accordance with Example I containing 0.175 units of heparin/ml of PPP and various quantities of the microspheres of Example II B and II C were prepared. Clot times observed with these microspheres are shown in FIG. 6. Curve A is a plot of clot time of the heparinized PPP by the spheres of II B (without thrombin) showing that heparinized PPP did not clot in the absence of thrombin. Curve B shows that, in the presence of surface-immobilized thrombin (Example II C), a surface-to-volume ratio in excess of $4.5 \times 10^{-3}$ $m^2$/ml was required to obtain clot time near 4 minutes whereas only $2 \times 10^{-3}$ $m^2$/ml was required for PPP with no added heparin (see curve C of FIG. 3). It can be inferred from this data that approximately half the immobilized thrombin activity was directed to neutralization of heparin anticoagulant properties.

EXAMPLE VI

This example demonstrates clotting activity by the dual pathway clotting enhancer of the invention prepared by crushing glass spheres bearing surface-immobilized thrombin.

Glass spheres bearing immobilized thrombin of Example II C were crushed using mortar and pestle. The crushed spheres were washed in saline solution to remove whole spheres and colloidal/particles by flotation. Surface area of the final product was determined to be 0.9 $m^2$/gm as measured by Krypton gas adsorption as in Example II. Crushing creates equal surface area of immobilized thrombin (outside sphere surface) and untreated glass (inside sphere surface).

Figure 7:
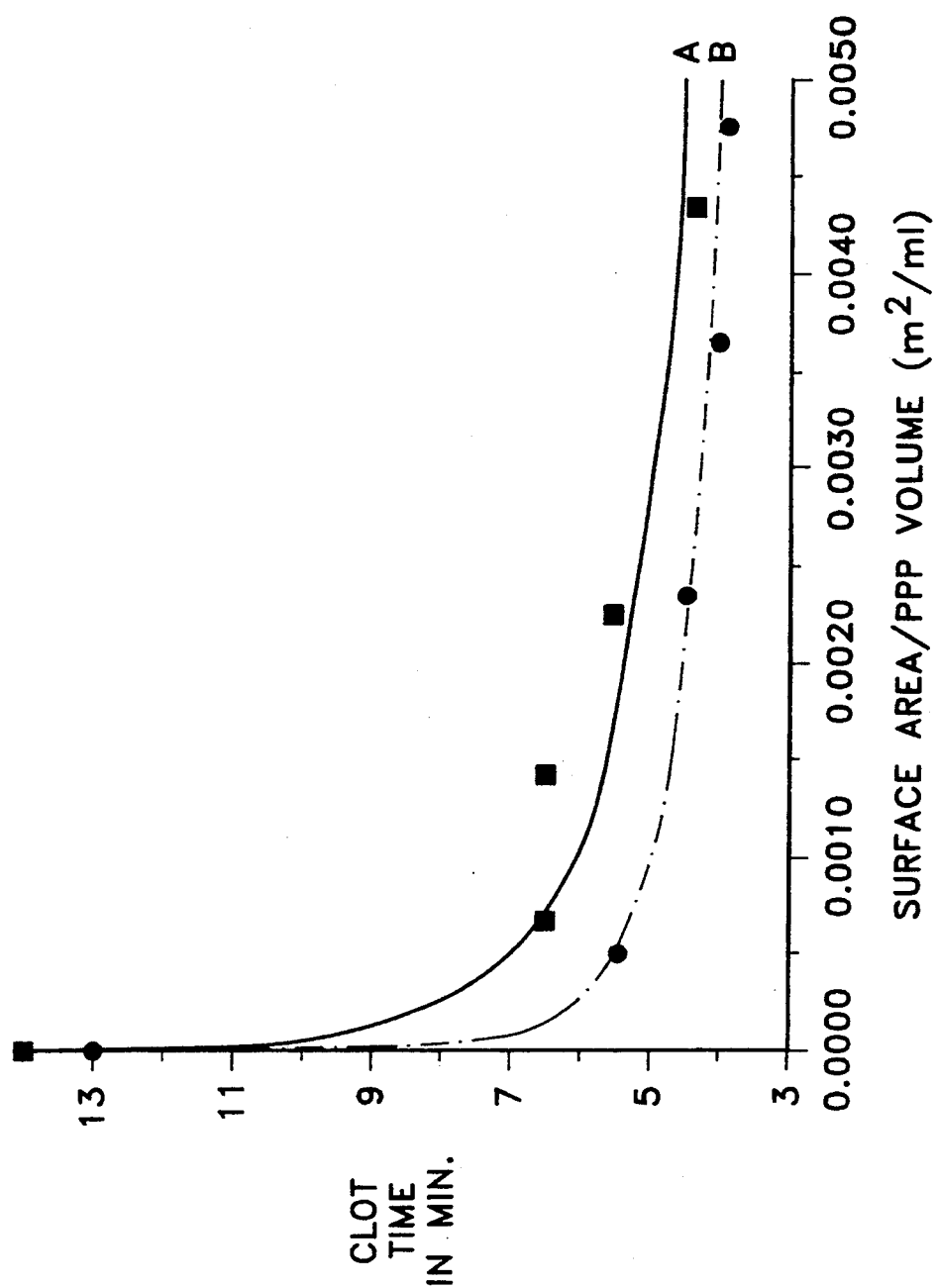

Clot activation by the dual pathway clotting enhancer was measured in PPP containing 0.175 units of heparin/ml for direct comparison to results of Example II C obtained with whole glass spheres bearing surface-immobilized thrombin. Curve A of FIG. 7 reproduces curve B of FIG. 6 showing clotting of heparinized PPP by surface-immobilized thrombin on whole spheres, and may be compared with results obtained with the same activator in crushed form (curve B of FIG. 7). It is seen that clot activation of the crushed form is greater than that of the whole sphere on an equivalent surface-area-to-volume ratio basis, and represents additional reduction in clot time due to activation of the intrinsic pathway of the coagulation cascade by the native glass surface exposed when the sphere was crushed.

What is claimed is:

1. A coagulation enhancing additive in a blood collection container comprising a plurality of glass particles, a first of said particles being unmodified so that the native glass surface activates the intrinsic coagulation pathway and a second of said particles being modified to have an activator of the extrinsic coagulation pathway immobilized on its surface.

2. The additive of claim 1 further comprising a coating of plastic on said second particle, said activator of the extrinsic coagulation pathway being immobilized on said coating of plastic.

3. A coagulation enhancing additive in a blood collection container comprising a particle having a plurality of surface areas, a first of said surface areas activating the intrinsic coagulation pathway and a second of said surface areas having immobilized thereon an activator of the extrinsic coagulation pathway.

4. The additive of claim 3 further comprising a layer of plastic between said second surface and said immobilized activator.

5. The additive of claim 4 wherein said activator of the extrinsic pathway is selected from the group consisting of ellagic acid and a protein.

6. The additive of claim 5 wherein said protein is a blood clotting factor of the extrinsic pathway.

7. The additive of claim 5 wherein said protein is a heparin antagonist which inactivates heparin in a heparinized blood sample so that said sample can be coagulated.

8. A blood collection assembly comprising:
a) a blood collection container having an open end;
b) a septum over said open end, said container being evacuated; and
c) the additive of claim 1 within said evacuated container.

9. A blood collection assembly comprising:
a) a blood collection container having an open end;
b) a septum over said open end, said container being evacuated; and
c) the additive of claim 3 within said evacuated container.

10. A blood collection assembly comprising:
a) a blood collection container having an open end and an interior wall surface;
b) a septum over said open end, said container being evacuated;
c) a first area of said interior wall surface which activates clotting of blood through the intrinsic coagualtion pathway; and
d) a second area of said interior wall surface which activates clotting of blood through the extrinsic coagualtion pathway.

* * * * *